United States Patent
Ignatyev et al.

(10) Patent No.: US 7,145,004 B2
(45) Date of Patent: Dec. 5, 2006

(54) METHOD FOR THE PRODUCTION OF MONOHYDRO-PERFLUOROALKANES, BIS(PERFLUOROALKYL)PHOSPHINATES AND PERFLUOROALKYLPHOSPHONATES

(75) Inventors: Nikolai Ignatyev, Duisburg (DE); Michael Weiden, Darmstadt (DE); Urs Welz-Biermann, Heppenheim (DE); Udo Heider, Winchester (GB); Peter Sartori, Utting (DE); Andriy Kucheryna, Duisburg (DE); Helge Willner, Muehlheim/Ruhr (DE)

(73) Assignee: Merck Patent Gesellschaft, Darmstadt (DE)

( * ) Notice: Subject to any disclaimer, the term of this patent is extended or adjusted under 35 U.S.C. 154(b) by 139 days.

(21) Appl. No.: 10/511,171

(22) PCT Filed: Mar. 17, 2003

(86) PCT No.: PCT/EP03/02744

§ 371 (c)(1),
(2), (4) Date: Oct. 14, 2004

(87) PCT Pub. No.: WO03/087111

PCT Pub. Date: Oct. 23, 2003

(65) Prior Publication Data
US 2005/0222411 A1    Oct. 6, 2005

(30) Foreign Application Priority Data
Apr. 16, 2002  (DE) ............................... 102 16 995
May 8, 2002    (DE) ............................... 102 20 547

(51) Int. Cl.
*C07D 237/00* (2006.01)
*C97D 237/02* (2006.01)

(52) U.S. Cl. ..................... 544/224; 544/242; 544/336; 546/347; 548/146; 548/215

(58) Field of Classification Search ................ 544/224, 544/242, 336; 546/347; 548/146, 215
See application file for complete search history.

(56) References Cited

OTHER PUBLICATIONS

Mahmood et al., New perfluoroalkylphosphonic and bis(perfluoroalkyl)phosphinic acids and their precursors, Inorg. Chem.; 1986; 25(18); 3128-3131.*
Pavlenko et al. Esters of Bis(perfluoroalkyl)phosphonic Acids, Journal of General Chemistry, USSR, 474-476.*
Kovaleva et al., Preparation perfluoroalkylphosphonic Acids And Their Derivatives, Journal of General Chemistry, USSR, 2245-2248.*
Kovaleva T.V. et al.: "Perfluoroalkylphosphonic Acids and Their Derivatives" Journal of General Chemistry USSR., Bd. 59, Nr. 11, Apr. 20, 1990, pp. 2245-2248.
Pavlenko N.V. et al.: "Esters of BIS (Perfluoroalkyl) Phosphinic Acids" Journal of General Chemistry USSR., Bd. 59, Nr. 3, Aug. 20, 1989, pp. 474-476.
Mahmood T et al.: "New Perfluoroalkylphosphonic and Bis (Perfluoroalkyl) Phosphinic Acids and Their Precursors" Inorganic Chemistry, American Chemical Society, Bd. 25, Nr. 18, 1986, pp. 3128-3131.
Gosling, K. et al: "Preparation and Hydrolysis of Tertiary Alkyl (Perfluoroalkyl) Phosphines" Journal of the Chemical Society 'Section! A: Inorganic, Physical, Theoretical 1968, p. 1914.
Haszeldine R.N.: "Reactions of Fluorocarbon Radicals. Part XII." Journal of the Chemical Society., 1953, pp. 3761-3768.
Bergman E.: "Decarbethoxylation of Perfluoroacid Esters" Journal of Organic Chemistry., Bd. 23, Nr. 3, 1958, pp. 476-477.

* cited by examiner

*Primary Examiner*—Thurman K. Page
*Assistant Examiner*—Chukwuma Nwaonicha
(74) *Attorney, Agent, or Firm*—Millen, White, Zelano & Branican, P.C.

(57) ABSTRACT

The present invention relates to a process for the preparation of monohydroperfluoroalkanes, bis(perfluoroalkyl)phosphinates and perfluoroalkylphosphonates which comprises at least the treatment of at least one perfluoroalkylphosphorane with at least one base in a suitable reaction medium.

23 Claims, No Drawings

METHOD FOR THE PRODUCTION OF MONOHYDRO-PERFLUOROALKANES, BIS(PERFLUOROALKYL)PHOSPHINATES AND PERFLUOROALKYLPHOSPHONATES

The present invention relates to a process for the preparation of monohydroperfluoroalkanes, bis(perfluoroalkyl) phosphinates and perfluoroalkylphosphonates which comprises at least the treatment of at least one perfluoroalkylphosphorane with at least one base in a suitable reaction medium.

Monohydroperfluoroalkanes have been known for some time and have found broad application in various areas, inter alia as ozone-friendly refrigerants (WO 01/40400, WO 01/23494, WO01/23491, WO99/36485, WO98/08913), as cleaning agents (WO 01/32323), as a constituent of etchants for the microelectronics area (US 2001/0005637, U.S. Pat. No. 6,228,775) in fire extinguishers (WO010/5468, Combust. Flame, 121, No. 3 (2000) pages 471–487, CN 1218702), as blowing agents in foams (U.S. Pat. No. 6,225, 365, WO 01/18098) and for the preparation of polymeric materials and potential anaesthetics (Anesth. Analg (N.Y.), 79, No. 2 (1994), pages 245–251, T. Hudlicky et al., J. of Fluorine Chem., 59, No. 1 (1992), pages 9–14).

Some of these monohydroperfluoroalkanes, such as, for example, pentafluoroethane, are already produced industrially on a tone scale, the production usually being carried out by catalytic hydrofluorination of chlorinated hydrocarbons (WO01/77048, EP 1052235).

Disadvantageous in teses processes is firstly the risk associated with the use of hydrogen fluoride at relatively high temperatures. Furthermore, the processes require particular catalysts, which have to be prepared in advance by comparatively complex processes. A further disadvantage of these processes is that the preparation of the chlorinated hydrocarbons using chlorine is ecologically dubious, and the production costs further increased. Finally, the known processes for the preparation of pentafluoroethane are not readily suitable for the preparation of longer-chain monohydroperfluoroalkanes, such as, for example, 1-hydrononafluorobutanes.

Furthermore, some further processes are known in which pentafluoroethane is prepared using special fluorinating agents, such as, for example, $BrF_3$ (R. A. Devis, J. Org. Chem. 32 (1967), page 3478), $XeF_2$ (JP2000/119201), $SF_4$ (G. Siegemund, Liebigs Ann. Chem., 1979, page 1280, E. R. Bissell, J. of Organic Chem., 29, (1964), page 1591), $SbF_5$ (G. G. Belenkii et al., Izv. Akad. Nauk SSSR, Ser. Khim., 1972, pages 983, Chem. Abstr. 77 (1972) 75296, A. F. Ermolov et al., Zh. Org. Khim., 17 (1981), page 2239, J. Org. Chem. USSR (Engl. Translation), 17 (1981), page 1999, U.S. Pat. No. 2,426,172), $MoF_6$ (L. D. Shustov et al., Zh. Obshch. Khim., 53 (1983), page 103, J. Gen. Chem. USSR (Engl. translation), 53 (1983), page 85) and $CoF_3$ (U.S. Pat. No. 6,162,955).

However, the above-mentioned processes have not achieved industrial significance since both the respective starting compounds and the fluorinating agents themselves are very expensive.

By contrast, only few processes are known for the preparation of long-chain monohydroperfluoroalkanes.

According to a first process, monohydroperfluoroalkanes are prepared by decarboxylation of salts of perfluorinated carboxylic acids (J. D. LaZerte et al., J. Am. Chem. Soc., 75 (1953), page 4525; R. N. Haszeldine, J. Chem. Soc. 1953, page 1548) or corresponding esters (E. Bergman, J. Org. Chem., 23, (1958) page 476) by treatment with strong bases, such as, for example, sodium ethoxide.

According to another process, monohydroperfluoroalkanes are prepared by treatment of perfluorinated ketones having a trifluoromethyl group on the carbonyl carbon atom with aqueous alkali (L. V. Saloutina et al., Izv. Akad. Nauk SSSR, Ser. Khim., 1984, No. 5, pages 1114–1116, Chem. Abstr. 101 (1984) 210504x). These processes also have the disadvantage of the use of expensive starting materials and the high temperatures necessary.

1-Hydro-n-nonafluorobutane is furthermore prepared by reduction of perfluorobutyl iodide using various reducing agents, such as, for example, zinc dust in methanol (T. Hudlicky et al., J. of Fluorine Chem., 59, No. 1 (1992), pages 9–14), sodium methoxide (J. L. Howell et al., J. of Fluorine Chem., 72, No. 1 (1995), pages 61–68), by hydrogen in the gas phase at high temperatures (EP 6 32 001), and with the aid of the thallium complex $[TaCp_2(C_2H_4)H]$ (P. H. Russel et al., Polyhedron 17, No. 7 (1998), pages 1037–1043).

However, these processes likewise have the disadvantage that they start from the starting compound perfluorobutyl iodide, which can only be prepared by comparatively expensive production processes.

The object of the present invention was therefore to provide a process which enables the simple and inexpensive preparation of monohydroperfluoroalkanes in good yields. The monohydroperfluoroalkanes should preferably be obtained in high purity. A further object was to prepare bis(perfluoroalkyl)phosphinates and perfluoroalkylphosphonates.

This object has been achieved by the process according to the invention for the preparation of monohydroperfluoroalkanes of the general formula $C_nHF_{2n+1}$, in which $1 \leq n \leq 8$, preferably $1 \leq n \leq 4$, bis(perfluoroalkyl)phosphinates and perfluoroalkylphosphonates which comprises at least the treatment of at least one perfluoroalkylphosphorane with at least one base in a suitable reaction medium.

In accordance with the invention, the preparation of monohydroperfluoroalkanes by the process according to the invention can in each case be carried out using a perfluoroalkylphosphorane or mixtures of two or more perfluoroalkylphosphoranes. Preferably, only one perfluoroalkylphosphorane is in each case reacted by the process according to the invention.

The perfluoroalkylphosphoranes used in the process according to the invention can be prepared by conventional methods known to the person skilled in the art.

The perfluoroalkylphosphoranes are preferably prepared by electrochemical fluorination of suitable starting compounds, as described in V. Ya. Semenii et al., Zh. Obshch. Khim., 55, No. 12 (1985), pages 2716–2720; N. Ignatiev, J. of Fluorine Chem., 103 (2000), pages 57–61 and WO 00/21969. The corresponding descriptions are incorporated herein by way of reference and are regarded as part of the disclosure.

In a preferred embodiment of the process according to the invention, use is made of at least one perfluoroalkylphosphorane of the general formula I

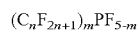

in which $1 \leq n \leq 8$, preferably $1 \leq n \leq 4$, and m in each case denotes 1, 2 or 3.

Particularly preferred perfluoroalkylphosphorane compounds are selected from the group consisting of difluorotris (pentafluoroethyl)phosphorane, difluorotris(n-nonafluorobutyl)phosphorane, difluorotris(n-heptafluoropropyl)-phosphorane and trifluorobis(n-nonafluorobutyl)phosphorane.

The treatment of the perfluoroalkylphosphorane compound(s) by the process according to the invention is preferably in each case carried out using only one base. It is of course however also possible to use mixtures of two or more bases in the process according to the invention. The respective bases can also be used in the form of corresponding solvates, preferably in the form of corresponding hydrates, or in the form of conventional adducts known to the person skilled in the art.

In a further preferred embodiment of the process according to the invention for the preparation of monohydroperfluoroalkanes, use is made of a base generally (a), preferably an inorganic base (b) or organic base (c). The inorganic base (b) is preferably selected from the group consisting of alkali metal hydroxides and alkaline earth metal hydroxides.

If an alkali metal hydroxide is used as base (b) in the process according to the invention, this can preferably be selected from the group consisting of lithium hydroxide, lithium hydroxide monohydrate, sodium hydroxide and potassium hydroxide.

If an alkaline earth metal hydroxide is used as base (b) in the process according to the invention, this can preferably be selected from the group consisting of barium hydroxide, barium hydroxide octahydrate and calcium hydroxide.

The process according to the invention for the preparation of monohydroperfluoroalkanes can likewise preferably be carried out using an organic base (c) or organometallic compounds. The base (c) can preferably be selected from the group consisting of alkylammonium hydroxides, arylammonium hydroxides, alkylarylammonium hydroxides, alkylphosphonium hydroxides, arylphosphonium hydroxides, alkylarylphosphonium hydroxides, alkylamines, arylamines, alkylarylamines, alkylphosphines, arylphosphines and alkylarylphosphines.

Preferred organometallic compounds can be selected from the group consisting of metal alkoxides, preferably alkali metal alkoxides, metal aryloxides, metal alkylthiooxides, metal arylthiooxides, alkylmetal compounds, arylmetal compounds and Grignard reagents.

If one of the above-mentioned classes of bases contains an alkyl radical, this can preferably contain from 1 to 4 carbon atoms. If the corresponding base contains two or more alkyl radicals, these may in each case be identical or different, identical alkyl radicals being preferred.

If one of the above-mentioned classes of bases contains an aryl radical, this can preferably be an unsubstituted or at least monosubstituted phenyl radical.

If an alkali metal alkoxide is used as base in the process according to the invention, this can preferably be derived from sodium and can preferably have from 1 to 3 carbon atoms.

Suitable reaction media for use in the process according to the invention are conventional reaction media which are known to the person skilled in the art so long as these do not undergo an irreversible chemical reaction with the respective base or the respective monohydroperfluoroalkane obtained.

In a further preferred embodiment of the process according to the invention, the reaction medium is water, if desired mixed with one or more organic solvents, where two-phase systems, such as, for example, mixtures of water and hydrocarbon, are also included in accordance with the invention.

The process according to the invention for the preparation of monohydroperfluoroalkanes can likewise preferably be carried out using one or more organic solvents, where, in the case where at least two solvents are used, these can, if desired, be in the form of a two-phase system.

Suitable organic solvents which are used in the process according to the invention, in each case alone or in any desired combination with one another, if desired also mixed with water, can preferably be selected from the group consisting of alcohols, ethers, acylamides, sulfoxides, sulfones, nitrites and hydrocarbons.

Preferred alcohols are those having from 1 to 4 carbons in the alkyl moiety. Corresponding alcohols can preferably be selected from the group consisting of methanol, ethanol, isopropanol and mixtures of at least two of these above-mentioned alcohols.

The amount of the monohydroperfluoroalkane formed from the respective perfluoroalkylphosphorane(s) employed and the type of the further reaction products can be controlled in a targeted manner in accordance with the process according to the invention, for example via the temperature and/or pressure during the reaction or via the molar ratio of perfluoroalkylphosphorane to base.

Through the choice of parameters, it is possible, for example, for one, two or three perfluoroalkyl groups to be cleaved off specifically from the respective difluorotrisperfluoroalkylphosphorane employed.

On removal of one perfluoroalkyl group from the respective difluorotrisperfluoroalkylphosphorane, the corresponding bis(perfluoroalkyl)phosphinate, inter alia, is also formed in addition to the desired monohydroperfluoroalkane.

On removal of two perfluoroalkyl groups from the respective difluorotrisperfluoroalkylphosphorane, the corresponding perfluoroalkylphosphonate, inter alia, is also formed in addition to the desired monohydroperfluoroalkane.

If all three perfluoroalkyl groups are removed from the respective difluorotrisperfluoroalkylphosphorane, the corresponding phosphate, inter alia, is also obtained in addition to the desired monohydroperfluoroalkane.

The respective choice of optimum parameters for the desired combination of the corresponding monohydroperfluoroalkane, the amount thereof and the respective further reaction products can be determined by the person skilled in the art by means of simple preliminary experiments.

If, for example, it is intended to remove one perfluoroalkyl group from the respective difluorotrisperfluoroalkylphosphorane employed, the process according to the invention can preferably be carried out at a temperature of from $-10°$ C. to $100°$ C. and a mole-equivalent ratio of difluorotrisperfluoroalkylphosphorane to base of 1:3.

If, for example, it is intended to remove two perfluoroalkyl groups from the respective difluorotrisperfluoroalkylphosphorane employed, the process according to the invention can preferably be carried out at a temperature of from $50°$ C. to $150°$ C. and a mole-equivalent ratio of difluorotrisperfluoroalkylphosphorane to base of 1:4.

If, for example, it is intended to remove the three perfluoroalkyl groups from the respective difluorotrisperfluoroalkylphosphorane employed, the process according to the invention can preferably be carried out at a temperature of from $100°$ C. to $250°$ C. and a mole-equivalent ratio of difluorotrisperfluoroalkylphosphorane to base of 1:5.

The monohydroperfluoroalkanes prepared by the process according to the invention can, if necessary, be isolated and, if necessary, purified by conventional methods known to the person skilled in the art.

If they are readily volatile compounds, they can be isolated from the reaction mixture by, for example, condensation in one or more cold traps, which are preferably cooled with liquid nitrogen or dry ice.

Any isolation and purification of further reaction products is likewise carried out by conventional methods known to the person skilled in the art, such as, for example, by fractional crystallisation or extraction with suitable solvents.

If the perfluoroalkylphosphorane is reacted with an inorganic base (b), the bis(perfluoroalkyl)phosphinates and perfluoroalkylphosphonates thus formed can be converted directly or after isolation using an acid, preferably using sulfuric acid, into the corresponding bis(perfluoroalkyl) phosphinic acids and perfluoroalkylphosphonic acids.

The bis(perfluoroalkyl)phosphinic acids and perfluoroalkylphosphonic acids obtained in this way can be converted into the salts by neutralisation, preferably using organic bases (c).

Through selection of suitable bases, the partially alkylated and peralkylated ammonium, phosphonium, sulfonium, pyridinium, pyridazinium, pyrimidinium, pyrazinium, imidazolium, pyrazolium, thiazolium, oxazolium and triazolium salts salts are preferably prepared.

Particular preference is given to the preparation of salts having a cation selected from the group consisting of

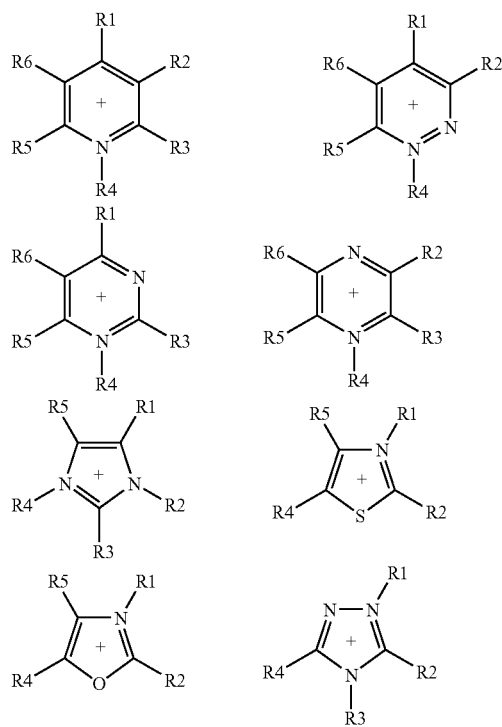

where $R^1$ to $R^5$ are identical or different, are optionally bonded directly to one another via a single or double bond and are each, individually or together, defined as follows:
H,
halogen, where the halogens are not bonded directly to N,
an alkyl radical ($C_1$ to $C_8$), which may be partially or completely substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)$, $C_nF_{(2n+1-x)}H_x$, where $1<n<6$ and $0<x\leq$ These salts can also be obtained if the salt formed after the reaction of the perfluoroalkylphosphorane with an inorganic base (b) is subjected to salt interchange, directly or after isolation.

The salt interchanges can be carried out with aryl-, alkyl- or alkylarylammonium or -phosphonium salts. Preference is given to the use of hexafluorophosphates, tetrafluoroborates, hexafluoroarsenates, sulfates, fluorides, chlorides or bromides.

The salts obtained in this way can be worked up in a conventional manner known to the person skilled in the art.

The process according to the invention for the preparation of monohydroperfluoroalkanes enables the simple, inexpensive and reliable preparation of these compounds in very good yields. In particular, the perfluoroalkylphosphoranes used as starting compounds can be prepared inexpensively in large quantities.

It is furthermore advantageous that the by-products obtained in the process according to the invention, such as, for example, the bis(perfluoroalkyl)phosphinates and perfluoroalkylphosphonates, are themselves valuable raw materials which are suitable, inter alia, for the preparation of the corresponding bis(perfluoroalkyl)phosphinic acids and perfluoroalkylphosphonic acids and thus can be utilised economically. Neutralisation using suitable bases enables preparation from them of, for example, bis(perfluoroalkyl)phosphinates and perfluoroalkylphosphonates, which are suitable for use as ionic liquids, surfactants or phase-transfer catalysts.

This furthermore has the advantage that the environmental impact in the reaction by the process according to the invention is kept small, which furthermore has a positive effect on the production costs of the monohydroperfluoroalkanes prepared by the process according to the invention.

The respective monohydroperfluoroalkanes are furthermore obtained in high purity immediately after their preparation, i.e. without complex purification steps.

The invention is explained below with reference to examples. These examples serve merely to explain the invention and do not restrict the general inventive idea.

EXAMPLES

Example 1

10.40 g (185.4 mmol) of potassium hydroxide are dissolved in 330 cm³ of water in a flask, and the resultant solution is cooled at a bath temperature of −5° C. 25.53 g (59.9 mmol) of difluorotris(pentafluoroethyl)phosphorane are subsequently added via a dropping funnel over the course of 15 minutes with stirring. The reaction mixture is subsequently brought to room temperature. The gaseous pentafluoroethane formed by alkaline hydrolysis of the difluorotris(pentafluoroethyl)phosphorane is collected in two subsequent traps, each of which is cooled with liquid nitrogen. 6.67 g of solid pentafluoroethane having a boiling point of −48° C. are obtained in the cooled traps. This value corresponds to that indicated in the literature by L. Conte et al. in J. Fluor. Chem., 38, (1988), pages 319–326.

The yield of pentafluoroethane is 92.8%, based on a pentafluoroethyl group removed from the difluorotris(pentafluoroethyl)phosphorane under these conditions.

The reaction mixture in the flask furthermore contains a solution of potassium bis(pentafluoroethyl)phosphinate ($(C_2F_5)_2P(O)OK$) and potassium fluoride. In order to isolate the potassium bis(pentafluoroethyl)phosphinate, firstly the excess potassium hydroxide is neutralised using a few drops of an aqueous hydrogen fluoride solution, and the water is removed under reduced pressure. The resultant solid residue is dried under reduced pressure at 120 Pa and a bath temperature of 100° C. for two hours.

Potassium bis(pentafluoroethyl)phosphinate is extracted from the dried residue using 150 cm³ of methanol. The methanol is subsequently distilled off under reduced pressure at 120 Pa, and the solid residue of potassium bis (pentafluoroethyl)phosphinate is dried. The yield is 19.0 g, corresponding to 93.2%, based on the difluorotris(pentafluoroethyl)phosphorane employed.

The pentafluoroethane is characterised by means of $^1$H- and $^{19}$F-NMR spectroscopy and the potassium bis(pentafluoroethyl)phosphinate by means of $^{19}$F- and $^{31}$P-NMR spectroscopy.

Pentafluoroethane

The $^1$H- and $^{19}$F-NMR spectra are recorded on a Bruker WP 80 SY spectrometer at a frequency of 80.1 MHz for $^1$H and 75.4 MHz for $^{19}$F and a temperature of −70° C. To this end, use is made of an FEP (fluoroethylene polymer) tube inside a thin-walled 5 mm NMR tube with an acetone-D$_6$ film as external lock and TMS or CCl$_3$F, dissolved in the acetone-D$_6$ film, as external reference.

$^1$H-NMR spectrum:
(acetone-D$_6$ film, reference TMS in the film, δ, ppm) 5.80 tq; $^2J_{H,F}$=52.3 Hz; $^3J_{H,F}$=2.1 Hz $^{19}$F-NMR spectrum:
(acetone-D$_6$ film, reference CCl$_3$F in the film, δ, ppm) −86.54 s (CF$_3$); −138.55 d (CHF$_2$); $^2J_{H,F}$=52.5 Hz The data obtained correspond to the values disclosed in the literature by M. D. Bartberger et al. in Tetrahedron, 53, No. 29 (1997), pages 9857–9880 and N. Ignatiev et al. in Acta Chem. Scand. 53, No. 12 (1999), pages 1110–1116.

Potassium bis(pentafluoroethyl)phosphinate
((C$_2$F$_5$)$_2$P(O)OK)

The $^{19}$F- and $^{31}$P-NMR spectra are recorded on a Bruker Avance 300 spectrometer at a frequency of 282.4 MHz for $^{19}$F and 121.5 MHz for $^{31}$P.

$^{19}$F-NMR spectrum:
(solvent acetone-D$_6$, internal reference CCl$_3$F, δ, ppm) −80.38 m (CF$_3$); −125.12 dm (CF$_2$); $^2J_{P,F}$=67.3 Hz $^{31}$P-NMR spectrum:
(solvent acetone-D$_6$, reference 85% by weight H$_3$PO$_4$ in D$_2$O, δ, ppm) 0.72 quin; $^2J_{P,F}$=67.2 Hz Example 2

5.99 g (142.8 mmol) of lithium hydroxide monohydrate are dissolved in 150 cm³ of water in a flask, and the resultant solution is cooled at a bath temperature of −10° C. 19.30 g (45.3 mmol) of difluorotris(pentafluoroethyl)phosphorane are subsequently added via a dropping funnel over the course of 15 minutes with stirring. The reaction mixture is subsequently brought to room temperature. The gaseous pentafluoroethane formed by hydrolysis of the difluorotris (pentafluoroethyl)phosphorane is collected in two subsequent traps, each of which is cooled with liquid nitrogen. 4.95 g of pentafluoroethane as a solid are obtained in the cooled traps. The yield of pentafluoroethane is 91.2%, based on the a pentafluoroethyl group removed from the difluorotris(pentafluoroethyl)phosphorane under these conditions.

The reaction mixture in the flask furthermore contains a solution of lithium bis(pentafluoroethyl)phosphinate ((C$_2$F$_5$)$_2$P(O)OLi) and lithium fluoride. In order to isolate the lithium bis(pentafluoroethyl)phosphinate, firstly the excess lithium hydroxide is neutralised using a few drops of an aqueous hydrogen fluoride solution, the precipitate of lithium fluoride is filtered off, and the water is removed under reduced pressure. The resultant white solid of lithium bis(pentafluoroethyl)phosphinate is dried under reduced pressure at 120 Pa and a bath temperature of 100° C. for two hours. 13.1 g of lithium bis(pentafluoroethyl)phosphinate containing about 2% by weight of lithium fluoride are obtained, corresponding to a yield of 93.7%, based on the difluorotris(pentafluoroethyl)phosphorane employed.

The pentafluoroethane is characterised by means of $^1$H- and $^{19}$F-NMR spectroscopy and the lithium bis(pentafluoroethyl)phosphinate by means of $^{19}$F- and $^{31}$P-NMR spectroscopy.

The chemical shifts determined for pentafluoroethane correspond to the values indicated in Example 1.

Lithium bis(pentafluoroethyl)phosphinate

The $^{19}$F- and $^{31}$P-NMR spectra are recorded on a Bruker Avance 300 spectrometer at a frequency of 282.4 MHz for $^{19}$F and 121.5 MHz for $^{31}$P.

$^{19}$F-NMR spectrum:
(solvent acetone-D$_6$, internal reference CCl$_3$F, δ, ppm) −80.32 m (CF$_3$); −125.08 dm (CF$_2$); $^2J_{P,F}$=72.6 Hz $^{31}$P-NMR spectrum:
(solvent acetone-D$_6$, reference 85% by weight H$_3$PO$_4$ 15% by weight D$_2$O in acetone-D$_6$, δ, ppm) 0.27 quin; $^2J_{P,F}$=72.7 Hz Example 3

4.1 g (73.1 mmol) of potassium hydroxide are dissolved in 150 cm³ of water in a flask, and the resultant solution is cooled at a bath temperature of 0° C. 16.87 g (23.2 mmol) of difluorotris(n-nonafluorobutyl)phosphorane are subsequently added via a dropping funnel over the course of 3 minutes with stirring. The reaction mixture is subsequently brought to room temperature, stirred at this temperature for eight hours and subsequently refluxed for a further eight hours. The gaseous 1H-nonafluoro-n-butane formed by hydrolysis of the difluorotris(n-nonafluorobutyl)phosphorane is collected in a subsequent trap cooled with dry ice. 3.63 g of liquid 1H-nonafluoro-n-butane having a boiling point of 14° C. are obtained in the cooled trap.

The yield of 1H-n-nonafluorobutane is 71.2%, based on an n-nonafluorobutyl group removed from the difluorotris (n-nonafluorobutyl)phosphorane under these conditions.

The solution remaining in the flask is separated from the viscous residue likewise remaining in the flask and neutralised using hydrochloric acid. In order to isolate the potassium bis(n-nonafluorobutyl)phosphinate, the water is removed under reduced pressure. The resultant solid residue is dried under reduced pressure at 120 Pa and a bath temperature of 100° C. for two hours. The dried residue is subsequently extracted with three portions of 50 cm³ of methanol each, the fractions are combined, the is subsequently distilled off under reduced pressure at 125 Pa, and the solid residue is dried. The yield of potassium bis(n-nonafluorobutyl)phosphinate is 7.88 g, corresponding to 62.9%, based on the difluorotris(n-nonafluorobutyl)phosphorane employed.

The 1H-n-nonafluorobutane is characterised by means of $^1$H- and $^{19}$F-NMR spectroscopy and the potassium bis(n-nonafluorobutyl)phosphinate by means of $^{19}$F- and $^{31}$P-NMR spectroscopy.

1H-Nonafluorobutane

The $^{1}$H- and $^{19}$F-NMR spectra are recorded on a Bruker WP 80 SY spectrometer at a frequency of 80.1 MHz for $^{1}$H and 75.4 MHz for $^{19}$F and a temperature of –60° C. To this end, use is made of an FEP (fluoroethylene polymer) tube inside a thin-walled 5 mm NMR tube with an acetone-$D_6$ film as external lock and TMS or $CCl_3F$, dissolved in the acetone-$D_6$ film, as external reference.

$^{1}$H-NMR SPECTRUM:
(acetone-$D_6$ film, reference TMS in the film, δ, ppm) 6.14 tt; $^{2}J_{H,F}$=52.0 Hz; $^{3}J_{H,F}$=5.0 Hz $^{19}$F-NMR spectrum:
(acetone-$D_6$ film, $CCl_3F$ in the film, δ, ppm) –81.31 t ($CF_3$); –127.93 m ($CF_2$); –131.06 m ($CF_2$); –137.92 dm ($CF_2$); $^{2}J_{H,F}$=52.0 Hz The data obtained correspond to the values disclosed in the literature publication by T. Hudlicky et al. in J. of Fluorine Chem., 59, No. 1 (1992), pages 9–14.

Potassium bis(n-nonafluorobutyl)phosphinate

The $^{19}$F- and $^{31}$P-NMR spectra are recorded on a Bruker Avance 300 spectrometer at a frequency of 282.4 MHz for $^{19}$F and 121.5 MHz for $^{31}$P.

$^{19}$F-NMR spectrum:
(solvent $D_2O$, reference $CF_3COOH$ in $D_2O$=76.53 ppm, δ, ppm) –82.69 tt ($CF_3$); –122.33 m ($CF_2$); –123.31 dm ($CF_2$); –127.46 tm ($CF_2$); $^{2}J_{P,F}$=79.5 Hz; $^{4}J_{F,F}$=9.6 Hz; $^{4}J_{F,F}$=12.0 Hz; $J_{F,F}$=1.5 Hz;

$^{31}$P-NMR spectrum:
(solvent $D_2O$, internal reference 85% by weight $H_3PO_4$, ppm) 4.81 quin; $^{2}J_{P,F}$=78.9 Hz Example 4

7.0 g (124.8 mmol) of potassium hydroxide are dissolved in 10 cm$^3$ of water in a flask, and the resultant solution is warmed at a bath temperature of 70–80° C. 12.18 g (16.8 mmol) of difluorotris(n-nonafluorobutyl)phosphorane are subsequently added via a dropping funnel over the course of 20 minutes with stirring. The reaction mixture is subsequently warmed at a bath temperature of 150° C. and stirred at this temperature for a further two hours.

The gaseous 1H-n-nonafluorobutane formed by hydrolysis of the difluorotris(n-nonafluorobutyl)phosphorane is collected in a subsequent trap cooled with dry ice.

6.12 g of liquid 1H-n-nonafluorobutane are obtained in the cooled trap. The yield of 1H-n-nonafluorobutane is 82.9%, based on the two n-nonafluorobutyl groups removed from the difluorotris(n-nonafluorobutyl)phosphorane under these conditions.

The residue remaining in the flask is dissolved in 50 cm$^3$ of water, and the excess potassium hydroxide is neutralised using aqueous hydrogen fluoride solution.

In order to isolate the dipotassium (n-nonafluorobutyl) phosphonate, the water is removed under reduced pressure. The resultant solid residue is dried under reduced pressure at 120 Pa and a bath temperature of 100° C. for two hours. The dipotassium (n-nonafluorobutyl)phosphonate $C_4F_9$ $P(O)(OK)_2$ is subsequently extracted from the dried residue using two portions of 50 cm$^3$ of methanol each, the fractions are combined, and the methanol is distilled off. The solid residue is subsequently dried under reduced pressure at 125 Pa. The yield of dipotassium (n-nonafluorobutyl)-phosphonate is 5.0 g, corresponding to a yield of 79.2%, based on the difluorotris(n-nonafluorobutyl)phosphorane employed.

The 1H-n-nonafluorobutane is characterised by means of $^{1}$H- and $^{19}$F-NMR spectroscopy and the dipotassium (n-nonafluorobutyl)phosphonate by means of $^{19}$F- and $^{31}$P-NMR spectroscopy.

The chemical shifts determined for 1H-n-nonafluorobutane correspond to the values indicated in Example 3.

Dipotassium (n-nonafluorobutyl)phosphonate
$C_4F_9P(O)(OK)_2$

The $^{19}$F- and $^{31}$P-NMR spectra are recorded on a Bruker Avance 300 spectrometer at a frequency of 282.4 MHz for $^{19}$F and 121.5 MHz for $^{31}$P.

$^{19}$F-NMR spectrum:
(solvent $D_2O$, reference $CF_3COOH$ in $D_2O$=76.53 ppm, δ, ppm) –81.64 tt ($CF_3$); –121.94 m ($CF_2$); –122.86 dm ($CF_2$); –126.66 tm ($CF_2$); $^{2}J_{P,F}$=68.9 Hz; $^{4}J_{F,F}$=9.6Hz; $^{4}J_{F,F}$=13.4 Hz; $J_{F,F}$=3.9 Hz $^{31}$P-NMR spectrum:
(solvent $D_2O$, reference 85% by weight $H_3PO_4$ in $D_2O$, δ, ppm) 4.00 tt; $J_{P,F}$=68.8 Hz; $^{3}J_{P,F}$=3.4 Hz Example 5

8.0 g (190.5 mmol) of lithium hydroxide monohydrate are suspended in 15 cm$^3$ of water in a flask, and the resultant suspension is warmed at a bath temperature of 70–80° C. 21.21 g (29.2 mmol) of difluorotris(n-nonafluorobutyl)phosphorane are subsequently added via a dropping funnel over the course of 30 minutes with stirring. The reaction mixture is subsequently warmed to a bath temperature of 150° C. and stirred at this temperature for a further two hours.

The gaseous 1H-n-nonafluorobutane formed by hydrolysis of the difluoro-tris(n-nonafluorobutyl)phosphorane is collected in a subsequent trap cooled with dry ice.

7.24 g of liquid 1H-n-nonafluorobutane are obtained in the cooled trap. The yield of 1H-n-nonafluorobutane is 56.3%, based on the two n-nonafluorobutyl groups removed from the difluorotris(n-nonafluorobutyl)phosphorane under these conditions.

The residue remaining in the flask is dissolved in 50 cm$^3$ of water, the excess lithium hydroxide is neutralised using aqueous hydrogen fluoride solution, and the lithium fluoride precipitate formed is filtered off. In order to isolate the dilithium (n-nonafluorobutyl)phosphonate $C_4F_9P(O)(OLi)_2$, the water is removed under reduced pressure. The resultant white solid is dried under reduced pressure at 120 Pa and a bath temperature of 100° C. for two hours. 8.0 g of dilithium n-nonafluorobutylphosphonate are obtained, corresponding to a yield of 87.8%, based on the difluorotris(n-nonafluorobutyl)phosphorane employed.

The 1H-n-nonafluorobutane is characterised by means of $^{1}$H- and $^{19}$F-NMR spectroscopy and the dilithium (n-nonafluorobutyl)phosphonate by means of $^{19}$F- and $^{31}$P-NMR spectroscopy.

The chemical shifts determined for 1H-n-nonafluorobutane correspond to the values indicated in Example 3.

Dilithium n-nonafluorobutylphosphonate

The $^{19}$F- and $^{31}$P-NMR spectra are recorded on a Bruker Avance 300 spectrometer at a frequency of 282.4 MHz for $^{19}$F and 121.5 MHz for $^{31}$P.

$^{19}$F-NMR spectrum:
(solvent $D_2O$, reference $CF_3COOH$ in $D_2O$=76.53 ppm, δ, ppm) –81.85 tt ($CF_3$); –122.03 m ($CF_2$); –123.06 dm ($CF_2$); –126.79 tm ($CF_2$); $^{2}J_{P,F}$=70.1 Hz; $^{4}J_{F,F}$=9.5 Hz; $^{4}J_{F,F}$=14.2 Hz; $J_{F,F}$=3.9 Hz (solvent acetone-$D_6$, internal reference $CCl_3F$, δ, ppm) −80.92 m ($CF_3$); −120.66 m ($CF_2$); −122.70 dm ($CF_2$); −125.62 tm ($CF_2$); $^2J_{P,F}$=78.6 Hz; $^4J_{F,F}$=9.9 Hz; $^4J_{F,F}$=14.5 Hz; $J_{F,F}$=3.2 Hz $^{31}$P-NMR spectrum:

(solvent $D_2O$, reference 85% by weight $H_3PO_4$ in $D_2O$, δ, ppm) 3.81 tt; $^2J_{P,F}$=70.1 Hz; $^3J_{P,F}$=3.3 Hz (solvent acetone-$D_6$, reference 85% by weight $H_3PO_4$—15% $D_2O$ in acetone-$D_6$, δ, ppm) −0.28 t; $^2J_{P,F}$=78.1 Hz Example 6

10.24 g (182.5 mmol) of potassium hydroxide are dissolved in 10 cm$^3$ of water in a flask, and the resultant solution is warmed at a bath temperature of 65-70° C. 18.70 g (43.9 mmol) of difluorotris(pentafluoroethyl)phosphorane are subsequently added via a dropping funnel over the course of 60 minutes with stirring. The reaction mixture is subsequently warmed at a bath temperature of 120° C. and stirred at this temperature for a further hour.

The gaseous pentafluoroethane formed by hydrolysis of the difluorotris(pentafluoroethyl)phosphorane is collected in a subsequent trap cooled with liquid nitrogen.

9.99 g of solid pentafluoroethane are obtained in the cooled trap. The yield of pentafluoroethane is 94.8%, based on the two pentafluoroethyl groups removed from the difluorotris(pentafluoroethyl)phosphorane under these conditions.

The residue remaining in the flask is dissolved in 40 cm$^3$ of water, and the excess potassium hydroxide is neutralised using a few drops of an aqueous hydrogen fluoride solution.

In order to isolate the dipotassium pentafluoroethylphosphonate, the water is removed under reduced pressure. The resultant solid is dried under reduced pressure at 120 Pa and a bath temperature of 100° C. for one hour. The dipotassium pentafluoroethylphosphonate is subsequently extracted from the solid residue using two portions of methanol of 50 cm$^3$ each, the fractions are combined, the methanol is distilled off, and the resultant residue is dried under reduced pressure at 120 Pa.

16.54 g of dipotassium pentafluoroethylphosphonate di(potassium fluoride) ($C_2F_5P(O)(OK)_2$).2KF are obtained, corresponding to a yield of 96.1%, based on the difluorotris(pentafluoroethyl)phosphorane employed.

The pentafluoroethane is characterised by means of $^1$H- and $^{19}$F-NMR spectroscopy and the dipotassium pentafluoroethylphosphonate di-(potassium fluoride) by means of $^{19}$F- and $^{31}$P-NMR spectroscopy.

The chemical shifts determined for pentafluoroethane correspond to the values indicated in Example 1.

Dipotassium pentafluoroethylphosphonate di(potassium fluoride)

$^{19}$F-NMR spectrum:

(solvent $D_2O$, reference $CF_3COOH$ in $D_2O$=76.53 ppm, δ, ppm) −81.86 t ($CF_3$); −125.91 q ($CF_2$); −122.70 s (2KF); $^2J_{P,F}$=68.4 Hz; $^3J_{F,F}$=1.6 Hz $^{31}$P-NMR spectrum:

(solvent $D_2O$, reference 85% by weight $H_3PO_4$ in $D_2O$, δ, ppm) 3.17 t; $^2J_{P,F}$=68.4 Hz Example 7

8.50 g (151.5 mmol) of potassium hydroxide are dissolved in 8.8 cm$^3$ of water in a flask, and the resultant solution is warmed at a bath temperature of 70–80° C. 15.77 g (37.0 mmol) of difluorotris(pentafluoroethyl)phosphorane are subsequently added via a dropping funnel over the course of 90 minutes with stirring.

The gaseous pentafluoroethane formed by hydrolysis of the difluorotris(pentafluoroethyl)phosphorane is collected in a subsequent trap cooled with liquid nitrogen.

8.30 g of solid pentafluoroethane are obtained in the cooled trap. The yield of pentafluoroethane is 93.4%, based on the two pentafluoroethyl groups removed from the difluorotris(pentafluoroethyl)phosphorane under these conditions.

The chemical shifts determined for pentafluoroethane correspond to the values indicated in Example 1.

Example 8

6.23 g (111.0 mmol) of potassium hydroxide are dissolved in 12.18 g of an ethanol/water mixture (1:1 parts by weight) in a flask, and the resultant solution is warmed at a bath temperature of 55–60° C. 11.43 g (26.8 mmol) of difluorotris(pentafluoroethyl)phosphorane are subsequently added via a dropping funnel over the course of 45 minutes with stirring, and the reaction mixture is heated at 80° C. for 10 minutes.

The gaseous pentafluoroethane formed by hydrolysis of the difluorotris(pentafluoroethyl)phosphorane is collected in a subsequent trap cooled with liquid nitrogen.

5.23 g of solid pentafluoroethane are obtained in the cooled trap. The yield of pentafluoroethane is 81.3%, based on the two pentafluoroethyl groups removed from the difluorotris(pentafluoroethyl)phosphorane under these conditions.

The chemical shifts determined for pentafluoroethane correspond to the values indicated in Example 1.

Example 9

13.46 g (31.6 mmol) of difluorotris(pentafluoroethyl) phosphorane are added via a dropping funnel over the course of one hour with stirring to 96.5 g (131.1 mmol) of a 20% by weight aqueous solution of tetraethylammonium hydroxide at room temperature.

Warming of the reaction mixture is observed during this operation. The reaction mixture is subsequently heated at 80° C. for 30 minutes. The gaseous pentafluoroethane formed by hydrolysis of the difluorotris(pentafluoroethyl) phosphorane is collected in a subsequent trap cooled with liquid nitrogen.

7.49 g of solid pentafluoroethane are obtained in the cooled trap. The yield of pentafluoroethane is 98.8%, based on the two pentafluoroethyl groups removed.

The chemical shifts determined for pentafluoroethane correspond to the values indicated in Example 1.

The solution remaining in the flask is evaporated on a rotary evaporator, and the resultant solid is dried under reduced pressure at 120 Pa and a temperature of 100° C., 24.67 g of white crystalline $[(C_2H_5)_4N]_2[C_2F_5PO_3]$.2 $[(C_2H_5)_4N]F.8H_2O$ The $[(C_2H_5)_4N]_2[C_2F_5PO_3]$.2 $[(C_2H_5)_4N]F.8H_2O$ is characterised by means of $^1$H-, $^{19}$F- and $^{19}F$ $^{31}$P-NMR spectroscopy and by elemental analysis:

The $^{19}$F-, $^1$H- and $^{31}$P-NMR spectra are recorded on a Bruker Avance 300 spectrometer at a frequency of 282.4 MHz for $^{19}$F and 121.5 MHz for $^{31}$P.

$^{19}$F-NMR spectrum:

(solvent acetonitrile-$D_3$, reference $CCl_3F$, δ, ppm) −79.41 dt ($CF_3$); −126.74 dq ($CF_2$); −111.74 (2F—); $^2J_{P,F}$=54.0 Hz; $^3J_{P,F}$=1.1 Hz; $^3J_{F,F}$=1.0 Hz $^1$H-NMR spectrum:

(solvent acetonitrile-D$_3$, reference TMS, δ, ppm) 1.21 tm (CH$_3$); 3.28 q (CH$_2$); $^3J_{H,H}$=7.3 Hz Proton exchange takes place between the H$_2$O molecules and the deuterium of the solvent;

$^{31}$P-NMR spectrum:

(solvent acetonitrile-D$_3$, reference 85% by weight H$_3$PO$_4$— 15% D$_2$O in acetonitrile-D$_3$, δ, ppm) −1.77 t; $^2J_{P,F}$=54.2 Hz Elemental analysis:

calculated for C$_{34}$H$_{96}$F$_5$N$_4$O$_{11}$P, C, 47.31%; H, 11.21%; N, 6.49% found: C, 47.37%; H, 10.80%; N, 6.40%.

Example 10

50.38 g (159.7 mmol) of barium hydroxide octahydrate are suspended in 100 cm$^3$ of water in a flask, and the resultant suspension is warmed at a bath temperature of 65–70° C. 22.68 g (53.2 mmol) of difluorotris(pentafluoroethyl)phosphorane are subsequently added via a dropping funnel over the course of 30 minutes with stirring. The reaction mixture is subsequently warmed to a temperature of 150° C. and stirred at this temperature for two hours.

The gaseous pentafluoroethane formed by hydrolysis of the difluorotris(pentafluoroethyl)phosphorane is collected in a subsequent trap cooled with dry ice.

10.00 g of liquid pentafluoroethane are obtained in the cooled trap. The yield of pentafluoroethane is 78.3%, based on the two pentafluoroethyl groups removed from the difluorotris(pentafluoroethyl)phosphorane under these conditions.

The residue remaining in the flask is taken up in 50 cm$^3$ of water and neutralised using an aqueous hydrogen fluoride solution. The barium fluoride precipitate formed is filtered off.

In order to isolate the barium pentafluoroethylphosphonate, the water is removed under reduced pressure. The resultant white solid is dried under reduced pressure at 120 Pa and a bath temperature of 100° C. for one hour. 10.6 g of barium pentafluorophosphonate ([C$_2$F$_5$P(O)O$_2$]Ba) containing about 2% by weight of barium fluoride are obtained, corresponding to a yield of 59.2%, based on the difluorotris (pentafluoroethyl)phosphorane employed.

The pentafluoroethane is characterised by means of $^1$H- and $^{19}$F-NMR spectroscopy and the barium pentafluorophosphonate by means of $^{19}$F- and $^{31}$P-NMR spectroscopy.

The chemical shifts determined for pentafluoroethane correspond to the values indicated in Example 1.

Barium pentafluoroethylphosphonate

The $^{19}$F-, $^1$H- and $^{31}$P-NMR spectra are recorded on a Bruker Avance 300 spectrometer at a frequency of 282.4 MHz for $^{19}$F and 121.5 MHz for $^{31}$P.

$^{19}$F-NMR spectrum:

(solvent D$_2$O, reference CF$_3$COOH in D$_2$O=76.53 ppm, δ, ppm) −81.99 td (CF$_3$); −126.25 dq (CF$_2$); J$_{P,F}$=70.5 Hz; J$_{F,F}$=1.8 Hz; J$_{P,F}$=0.5 Hz $^{31}$P-NMR spectrum:

(solvent D$_2$O, reference 85% by weight H$_3$PO$_4$ in D$_2$O, δ, ppm) 2.88 t; $^2J_{P,F}$=70.3 Hz Example 11

16.70 g (52.9 mmol) of barium hydroxide octahydrate are suspended in 20 cm$^3$ of water in a flask, and the resultant suspension is warmed at a bath temperature of 70–80° C. 17.79 g (24.5 mmol) of difluorotris(n-nonafluorobutyl)phosphorane are subsequently added with the aid of a dropping funnel over the course of 30 minutes with stirring. The reaction mixture is subsequently warmed at a bath temperature of 120° C. and stirred at this temperature for one hour.

The gaseous 1H-n-nonafluorobutane formed by hydrolysis of the difluorotris(n-nonafluorobutyl)phosphorane is collected in a subsequent trap cooled with liquid nitrogen.

7.72 g of solid 1H-n-nonafluorobutane are obtained in the cooled trap. The yield of 1H-n-nonafluorobutane is 71.6%, based on the two n-nonafluorobutyl groups removed from the difluorotris(n-nonafluorobutyl)phosphorane under these conditions.

The residue remaining in the flask is taken up in 50 cm$^3$ of water and neutralised using an aqueous hydrogen fluoride solution. The barium fluoride precipitate formed is filtered off.

In order to isolate the barium n-nonafluorobutylphosphonate, the water is removed under reduced pressure. The resultant white solid is dried under reduced pressure at 120 Pa and a bath temperature of 100° C. for one hour. 7.0 g of barium n-nonafluorobutylphosphonate ([n-C$_4$F$_9$P(O)O$_2$]Ba) containing about 2% by weight of barium fluoride are obtained, corresponding to a yield of 64.87%, based on the difluorotris(pentafluoroethyl)phosphorane employed.

The 1H-n-nonafluorobutane is characterised by means of $^1$H- and $^{19}$F-NMR spectroscopy and the barium n-nonafluorobutylphosphonate by means of $^{19}$F- and $^{31}$P-NMR spectroscopy.

The chemical shifts determined for 1H-nonafluorobutane correspond to the values indicated in Example 3.

Barium n-nonafluorobutylphosphonate $^{19}$F-NMR spectrum:

(solvent D$_2$O, reference CF$_3$COOH in D$_2$O=76.53 ppm, δ, ppm) −81.77 tt (CF$_3$); −122.29 m (CF$_2$); −123.66 dtm (CF$_2$); −126.76 tm (CF$_2$); $^2J_{P,F}$=75.8 Hz; $^4J_{F,F}$=9.7 Hz; $^4J_{F,F}$=13.8 Hz; J$_{F,F}$=3.6 Hz $^{31}$P-NMR spectrum:

(solvent D$_2$O, reference 85% by weight H$_3$PO$_4$ in D$_2$O, δ, ppm) 2.22 t; $^2J_{P,F}$=76.1 Hz Example 12

10.32 g (183.9 mmol) of potassium hydroxide and 20 cm$^3$ of water are introduced into an autoclave having a capacity of 100 cm$^3$. The autoclave is cooled to −30° C., and 9.70 g (22.8 mmol) of difluorotris(pentafluoroethyl)phosphorane are added. The autoclave is subsequently closed and heated at 200–210° C. for eight hours with the aid of an oil bath. The autoclave is then brought to room temperature, and an outlet of the autoclave is connected to a cold trap cooled with liquid nitrogen. 7.57 g of pure pentafluoroethane are obtained, corresponding to a yield of 92.2%, based on the three pentafluoroethyl groups removed from the difluorotris (pentafluoroethyl)phosphorane employed under these conditions.

The chemical shifts determined for the pentafluoroethane correspond to the values indicated in Example 1.

Example 13

51.0 g of potassium hydroxide and 50 cm$^3$ of water are introduced into an autoclave having a capacity 350 cm$^3$. The autoclave is cooled to −30° C., and 95.9 g of a mixture of trifluorobis(n-nonafluorobutyl)phosphorane (60 mol %) and difluorotris(n-nonafluorobutyl)phosphorane (40 mol %) are added. The autoclave is subsequently closed and heated at 200-210° C. for 18 hours with the aid of an oil bath. The autoclave is then brought to room temperature, and an outlet of the autoclave is connected to a cold trap cooled with dry ice.

68.0 g of pure 1H-nonafluoro-n-butane are obtained, corresponding to a yield 95.2%, based on the two n-nonafluorobutyl groups removed from the trifluorobis(n-nonafluorobutyl)phosphorane and difluorotris(n-nonafluorobutyl)phosphorane employed under these conditions.

The 1-H-nonafluoro-n-butane is characterised by means of $^1$H- and $^{19}$F-NMR spectroscopy.

The chemical shifts determined for 1H-nonafluoro-n-butane correspond to the values indicated in Example 3.

Example 14

Bis(pentafluoroethyl)phosphinic acid 4.09 g (12.0 mmol) of potassium bis(pentafluoroethyl)phosphinate are introduced into a distillation flask with 8.71 g (88.9 mmol) of 100% sulfuric acid $H_2SO_4$, and the resultant bis(pentafluoroethyl)phosphinic acid is distilled off under reduced pressure (400 Pa) and an oil-bath temperature 90-120° C. 3.25 g of a transparent and colourless liquid of bis(pentafluoroethyl)phosphinic acid, $(C_2F_5)_2P(O)OH$, are obtained, corresponding to a yields of 89.5%.

The values of the chemical shifts found correspond to the values disclosed in the publication by T. Mahmood, Inorganic Chemistry, 25 (1986), pages 3128–3131.

Example 15

1.0 g (10.2 mmol) of 100% sulfuric acid $H_2SO_4$ are added to a stirred solution of 3.42 g (10.2 mmol) of barium pentafluoroethylphosphonate in 50 cm$^3$ of water. A precipitate of barium sulfate is formed, which is separated off by filtration. The resultant filtrate is evaporated completely under reduced pressure and dried at 125 Pa and an oil-bath temperature of 100° C. for a further 6 hours. 1.75 g of a highly viscous liquid of pentafluoroethylphosphonic acid $C_2F_5P(O)(OH)_2$ are obtained, corresponding to a yield of 83.8%.

$^{19}$F-NMR spectrum:

(solvent: acetonitrile-D$_3$, reference CCl$_3$F, δ, ppm) −81.03 t (CF$_3$); −126.74 dq (CF$_2$); $J^2_{P,F}$=89.4 Hz, $J^3_{F,F}$=1.6 Hz.

$^1$H-NMR spectrum:

(solvent: acetonitrile-D$_3$, reference TMS, δ, ppm) 11.26 br.s (OH)

$^{31}$P-NMR spectrum (solvent: acetonitrile-D$_3$; reference: 85% by weight H$_3$PO$_4$— 15% by weight D$_2$O in acetonitrile-D$_3$): —3.40 t, $J^2_{P,F}$=89.6 Hz.

These data correspond to the values disclosed in the literature publication by T. Mahmood and J. M. Shreeve, in Inorg. Chem., 25 (1986), pages 3128–3131.

Example 16

A solution of 0.492 g (2.46 mmol) of pentafluoroethylphosphonic acid prepared as described in Example 15 in 10 cm$^3$ of water is neutralised using 3.015 g of 20% by weight aqueous tetraethylammonium hydroxide by slow addition at room temperature with stirring. The water is evaporated off under reduced pressure, and the resultant residue is dried under reduced pressure of 120 Pa and a bath temperature of 50° C. for 2 hour. 1.115 g of a white solid of bis(tetraethylammonium)pentafluoroethylphosphonate are obtained. The yield is 99.0%, based on the pentafluoroethylphosphonic acid employed.

Bis(tetraethylammonium)pentafluoroethylphosphonate was characterised by means of $^{19}$F, $^{31}$P and $^1$H-NMR spectroscopy.

$^{19}$F NMR spectrum, ppm:

(solvent: acetonitrile-D$_3$; reference: CCl$_3$F): −79.49 s (CF$_3$); −122.10 d (CF$_2$); $J^2_{P,F}$=54.6 Hz.

$^1$H NMR spectrum, ppm:

(solvent: acetonitrile-D$_3$; reference: TMS): 1.20 tm (12H, 4CH$_3$); 3.29 q (8H, 4CH$_2$); $J^3_{H,H}$=7.3 Hz.

$^{31}$P NMR spectrum, ppm:

(solvent: acetonitrile-D$_3$; reference: 85% H$_3$PO$_4$): −2.28 t; $J^2_{P,F}$=54.9 Hz.

Example 17

A solution of nonafluoro-n-butylphosphonic acid, prepared as described in Example 15 from 3.73 g (8.57 mmol) of barium nonafluoro-n-butylphosphonate and 0.839 g of 100% by weight sulfuric acid in 20 cm$^3$ of water, is neutralised (pH=7) using 20% by weight aqueous tetraethylammonium hydroxide by slow addition at room temperature with stirring. The water is evaporated off under reduced pressure, and the resultant residue is dried under reduced pressure of 120 Pa and a bath temperature of 60° C. for 2 hour.

4.59 g of solid of bis(tetraethylammonium) nonafluoro-n-butylphosphonate are obtained. The yield is 96.0%, based on the barium nonafluoro-n-butylphosphonate employed.

Bis(tetraethylammonium) nonafluoro-n-butylphosphonate was characterised by means of $^{19}$F, $^{31}$P and $^1$H-NMR spectroscopy:

$^{19}$F NMR spectrum, ppm:

(solvent: acetonitrile-D$_3$; reference: CCl$_3$F): −80.37 tt (CF$_3$); −119.57 m (CF$_2$); −119.72 dm (CF$_2$); −124.80 m (CF$_2$); $J^2_{P,F}$=55.6 Hz; $J^3_{F,F}$=4.3 Hz; $J^4_{F,F}$=9.5 Hz.

$^1$H NMR spectrum, ppm:

(solvent: acetonitrile-D$_3$; reference: TMS): 1.23 tm (12H, 4CH$_3$); 3.27 q (8H, 4CH$_2$); $J^3_{H,H}$=7.4 Hz.

$^{31}$P NMR spectrum, ppm:

(solvent: acetonitrile-D$_3$; reference: 85% H$_3$PO$_4$): −2.06 t; $J^2_{P,F}$=56.5 Hz.

Example 18

1.43 g of the pentafluoroethylphosphonic acid prepared as described in Example 15 are dissolved in 15 cm$^3$ of water and neutralised (pH=7) using 10% by weight aqueous potassium hydroxide by slow addition at room temperature with stirring. A solution of 2.09 g (11.9 mmol) of 1-ethyl-3-methylimidazolium chlorides in 3 cm$^3$ of water is added at room temperature to the resultant aqueous solution of dipotassium pentafluoroethylphosphonate with constant stirring. The water is evaporated off under reduced pressure, and the resultant residue is dried under reduced pressure of 120 Pa and a bath temperature of 60° C. for 1 hour. 10 cm$^3$ Of isopropyl alcohol are subsequently added to the residue, and a white precipitate is filtered off and washed twice with 5 cm$^3$ of isopropyl alcohol. The isopropyl alcohol is evaporated off under reduced pressure, and the resultant residue is dried under reduced pressure of 1.4 Pa and a bath temperature of 80° C. for 1.5 hour.

2.56 g of an oily liquid of di(1-ethyl-3-methylimidazolium)pentafluoroethylphosphonate are obtained. The yield is 85.0%, based on the pentafluoroethylphosphonic acid employed.

Di(1-ethyl-3-methylimidazolium)pentafluoroethylphosphonate is characterised by means of $^{19}$F, $^{31}$P and $^{1}$H-NMR spectroscopy:

$^{19}$F NMR spectrum, ppm:
(solvent: acetonitrile-D$_3$; reference: CCl$_3$F): −79.68 s (CF$_3$); −123.22 d (CF$_2$); $J^2_{P,F}$=57.9 Hz.

$^{1}$H NMR spectrum, ppm:
(solvent: acetonitrile-D$_3$; reference: TMS): 1.38 t (3H, CH$_3$); 3.94 s (3H, CH$_3$); 4.29 q (2H, CH$_2$); 7.70 s (1H); 7.75 s (1H); 10.82 s (1H); $J^3_{H,H}$=7.2 Hz.

$^{31}$P NMR spectrum, ppm:
(solvent: acetonitrile-D$_3$; reference: 85% H$_3$PO$_4$): −1.28 t; $J^2_{P,F}$=57.4 Hz.

Example 19

A solution 2.4 g (12.0 mmol) of pentafluoroethylphosphonic acid prepared as described in Example 15 in 13 cm$^3$ of water is neutralised (pH=7) using 14.86 g of approximately 40% by weight aqueous tetrabutylphosphonium hydroxide by slow addition at room temperature with stirring. The water is evaporated off under reduced pressure, and the resultant residue is dried under reduced pressure of 1.4 Pa and a bath temperature of 70° C. for 2 hour.

7.95 g of a highly viscous liquid are obtained, which slowly crystallises as a white solid bis(tetrabutylphosphonium)pentafluoroethylphosphonate. The yield is 92.4%, based on the pentafluoroethylphosphonic acid employed.

The melting point is 76-79° C.

Bis(tetrabutylphosphonium)pentafluoroethylphosphonate, [(C$_4$H$_9$)$_4$P$^+$]$_2$ C$_2$F$_5$P(O)O$_2^{2-}$, is characterised by means of $^{19}$F, $^{31}$P and $^{1}$H-NMR spectroscopy:

$^{19}$F NMR spectrum, ppm:
(solvent: acetonitrile-D$_3$; reference: CCl$_3$F): −79.39 s (CF$_3$); −121.98 d (CF$_2$) $J^2_{P,F}$=54.2 Hz.

$^{1}$H NMR spectrum, ppm:
(solvent: acetonitrile-D$_3$; reference: TMS): 0.93 t (12H, 4CH$_3$); 1.45 m (16H, 8CH$_2$); 2.37 m (8H, 4CH$_2$); $J^3_{H,H}$=7.1 Hz.

$^{31}$p NMR spectrum, ppm:
(solvent: acetonitrile-D$_3$; reference: 85% H$_3$PO$_4$): −1.84 t (1P); 32.73 m (2P); $J^2_{P,F}$=54.6 Hz.

The invention claimed is:

1. A process for preparing a monohydroperfluoroalkane, bis(perfluoroalkyl)phosphinate or perfluoroalkylphosphonate comprising treating a perfluoroalkylphosphorane with
    a) an alkaline earth metal hydroxide,
    b) an organometallic compound, or
    c) an organic base,
and optionally treating with, an acid in a reaction medium.

2. A process according to claim 1, wherein the perfluoroalkylphosphorane is reacted with an alkaline earth metal hydroxide in a solvent, the resultant bis(perfluoroalkyl)phosphinates and perfluoroalkylphosphonates in addition to the monohydroperfluoroalkanes are converted into the corresponding bis(perfluoroalkyl)phosphinic acids and perfluoroalkylphosphonic acids directly or after isolation by salt interchange or subsequent treatment with an acid, and salts are obtained by subsequent neutralisation.

3. A process according to claim 1, wherein the perfluoroalkylphosphorane is a compound of formula I

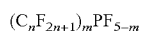
$(C_nF_{2n+1})_mPF_{5-m}$ in which 1≦n≦8, and m in each case denotes 1, 2 or 3.

4. A process according to claim 1, wherein the perfluoroalkylphosphorane is, difluorotris(pentafluoroethyl)phosphorane, difluorotris(n-nonafluorobutyl)phosphorane difluorotris(n-heptafluoropropyl)phosphorane or trifluorobis(n-nonafluorobutyl)phosphorane.

5. A process according to claim 1, wherein the organic base is selected from alkylammonium hydroxides, arylammonium hydroxides, alkylarylammonium hydroxides, alkylphosphonium hydroxides, arylphosphonium hydroxides, alkylarylphosphonium hydroxides alkylamines, arylamines, alkylarylamines, alkylphosphines, arylphosphines and alkylarylphosphines.

6. A process according to claim 1, wherein the alkaline earth metal hydroxide is barium hydroxide, barium hydroxide octahydrate or calcium hydroxide.

7. A process according to claim 1, wherein the organometallic compound is selected from metal alkoxides, alkali metal alkoxides, metal aryloxides, metal alkylthiooxides, metal arylthiooxides, alkylmetal compounds, arylmetal compounds and Grignard reagents.

8. A process according to claim 1, the reaction medium is water, optionally mixed with one or more organic solvents.

9. A process according to claim 1, wherein the reaction medium is one or more organic solvents.

10. A process according to claim 8, wherein the organic solvent is selected from alcohols, ethers, acylamides, sulfoxides, sulfones, nitriles and hydrocarbons.

11. A process according to claim 10, wherein the alcohol has one to four carbon atoms in an alkyl moiety.

12. A perfluoroalkylphosphonate or bis(perfluoroal)kylphosphinate selected from partially alkylated and peralkylated, phosphonium, sulfonium, pyridinium, pyridazinium, pyrimidinium, pyrazinium, imidazolium, pyrazolium, thiazolium, oxazolium and triazolium salts.

13. A perfluoroalkylphosphonate or bis(perfluoroalkyl) phosphinate according to claim 12, having a cation selected from

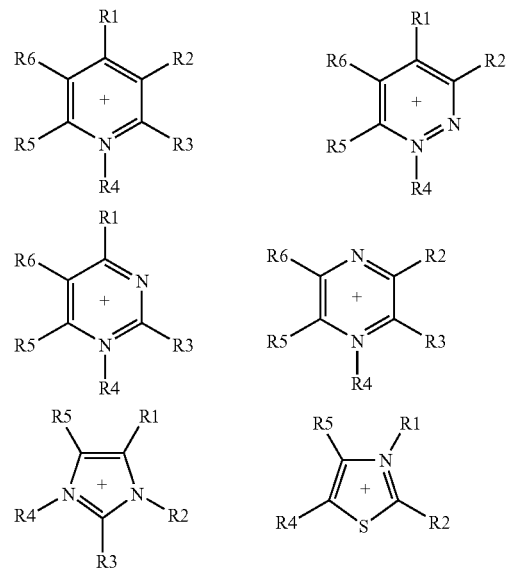

-continued

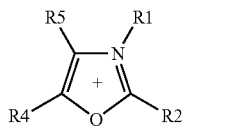
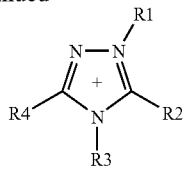
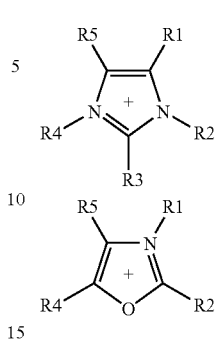
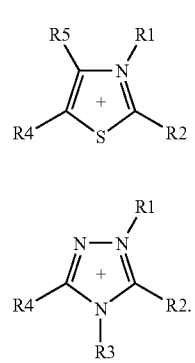

where $R^1$ to $R^6$ are identical or different, are optionally bonded directly to one another via a single or double bond and are each, individually or together, defined as follows:

H, halogen, where the halogens are not bonded directly to N, an $C_1$ to $C_8$ alkyl radical, which may be partially or completely substituted.

14. An ionic liquid comprising a perfluoroalkylphosphonate or bis(perfluoroalkyl)phosphinate according to claim 12.

15. A phase-transfer catalyst or surfactant comprising a perfluoroalkylphosphonate or bis(perfluoroalkyl)phosphinate according to claim 12.

16. A perfluoroalkylphosphonate or bis(perfluoroal)kylphosphinate according to claim 13, where $R^1$ to $R^6$ are identical or different, are optionally bonded directly to one another via a single or double bond and are each, individually or together, defined as follows:

H, halogen, where the halogens are not bonded directly to N, or an $C_1$ to $C_8$ alkyl radical, which may be partially or completely substituted by F, Cl, $N(C_nF_{(2n+1-x)}H_x)_2$, $O(C_nF_{(2n+1-x)}H_x)$, $SO_2(C_nF_{2n+1-x}H_x)$, $C_nF_{2n+1-x}H_x$), where 1<n<6 and 0<x $\leq$ 2n+1.

17. A perfluoroalkylphosphonate or bis(perfluoroal)kylphosphinate according to claim 13, having a cation selected from 18. A perfluoroalkylphosphonate or bis(perfluoroal)kylphosphinate according to claim 17, where $R^1$ to $R^5$ are identical or different, are optionally bonded directly to one another via a single or double bond and are each, individually or together, defined as follows:

H, halogen, where the halogens are not bonded directly to N, or an $C_1$ to $C_8$ alkyl radical, which may be partially or completely substituted by F, Cl, $N(C_nF_{(2n+1-x)}H_x)_2$, $O(C_nF_{(2n+1-x)}H_x)$, $SO_2(C_nF_{2n+1-x}H_x)$, $C_nF_{2n+1-x}H_x$), where 1<n<6 and 0<x $\leq$ 2n+1.

19. A process according to claim 4, in which $1 \leq n \leq 4$.

20. A process according to claim 10 wherein the alcohol is methanol, ethanol, isopropanol or a mixture thereof.

21. A process according to claim 1, wherein a perfluoroalkylphosphonate is obtained.

22. A process according to claim 1, wherein a bis(perfluoroalkyl)phosphinate is obtained.

23. A process according to claim 1, wherein a monohydroperfluoroalkane is obtained.

* * * * *

UNITED STATES PATENT AND TRADEMARK OFFICE
CERTIFICATE OF CORRECTION

PATENT NO. : 7,145,004 B2
APPLICATION NO. : 10/511171
DATED : December 5, 2006
INVENTOR(S) : Nikolai Ignatyev It is certified that error appears in the above-identified patent and that said Letters Patent is hereby corrected as shown below:

On the Title page, and col. 1 Title: line 1, reads "METHOD FOR THE PRODUCTION" should read -- PROCESS FOR THE PREPARATION --
Column 17, line 53, reads "with, an acid" should read -- with an acid --
Column 18, line 2, reads "is," should read -- is --
Column 18, line 3, reads "phosphorane difluorotris" should read -- phosphorane, difluorotris --
Column 18, line 24, reads "claim 1, the" should read -- claim 1, wherein the --
Column 18, line 35-36, reads "peralkylated, phosphonium" should read -- peralkylated phosphonium --
Column 19, line 37, reads "$C_nF_{2n+1-x}H_x$)," should read -- $C_nF_{(2n+1-x)}H_x$, --
Column 20, line 28, reads "$SO_2(C_nF_{2n+1-x}H_x), C_nF_{2n+1-x}H_x$)," should read -- $SO_2(C_nF_{(2n+1-x)}H_x), C_nF_{2n+1-x}H_x$, --
Column 20, line 31, reads "according to claim 10," should read -- according to claim 11, --

Signed and Sealed this

Nineteenth Day of June, 2007

JON W. DUDAS
*Director of the United States Patent and Trademark Office*